US009291691B2

(12) United States Patent
Amadon et al.

(10) Patent No.: US 9,291,691 B2
(45) Date of Patent: Mar. 22, 2016

(54) METHOD AND APPARATUS FOR COMPENSATING FOR $B_1$ INHOMOGENEITY IN MAGNETIC RESONANCE IMAGING BY NONSELECTIVE TAILORED RF PULSES

(75) Inventors: Alexis Amadon, Villiers-Saint-Frédéric (FR); Martijn Cloos, Gometz la Ville (FR)

(73) Assignee: Commissariat a l'Emergie Atomique et aux Energies Alternatives, Paris (FR)

( * ) Notice: Subject to any disclaimer, the term of this patent is extended or adjusted under 35 U.S.C. 154(b) by 567 days.

(21) Appl. No.: 13/126,922

(22) PCT Filed: Apr. 12, 2011

(86) PCT No.: PCT/IB2011/051581
§ 371 (c)(1),
(2), (4) Date: Jun. 30, 2012

(87) PCT Pub. No.: WO2011/128847
PCT Pub. Date: Oct. 20, 2011

(65) Prior Publication Data
US 2013/0038326 A1    Feb. 14, 2013

(30) Foreign Application Priority Data
Apr. 15, 2010  (EP) .................................. 10290205

(51) Int. Cl.
*G01V 3/00*    (2006.01)
*G01R 33/483*  (2006.01)
(Continued)

(52) U.S. Cl.
CPC .......... *G01R 33/4836* (2013.01); *G01R 33/246* (2013.01); *G01R 33/4818* (2013.01);
(Continued)

(58) Field of Classification Search
CPC .................................................. G01R 33/4818
USPC ........................................ 324/309, 307, 314
See application file for complete search history.

(56) References Cited

U.S. PATENT DOCUMENTS

| 8,938,281 B2 * | 1/2015 | Fuderer et al. ................ 600/410 |
| 2007/0057673 A1 | 3/2007 | Nayak et al. |
| 2010/0066362 A1 | 3/2010 | Ullmann |
| 2015/0042335 A1 * | 2/2015 | Nehrke et al. ................ 324/309 |

OTHER PUBLICATIONS

Search Report for European Application No. EP 10 29 0205, completed Sep. 21, 2010.
(Continued)

*Primary Examiner* — Louis Arana
(74) *Attorney, Agent, or Firm* — Alston & Bird LLP

(57) ABSTRACT

A method of exciting nuclear spins in a body, the method comprising the steps of: (a) immerging said body (PB) in a static magnetic field ($B_0$) for aligning nuclear spins along a magnetization axis (z), said static magnetic field being substantially uniform over at least a volume of interest (VOI) of said body; (b) exposing said body, or at least said volume of interest, to a time-varying magnetic field gradient having components ($G_x$, $G_y$, $G_z$) directed along at least three non-coplanar directions (x, y, z) and to a transverse radio-frequency field ($B_1$), whereby said time-varying magnetic field gradient defines a three-dimensional trajectory in k-space constituted by segments linking discrete points ($k_T^1$-$k_T^9$), and said transverse radio-frequency field deposits radio-frequency energy along at least part of said trajectory for flipping said nuclear spins by a same predetermined flip angle, independently from their position within said volume of interest. A method of performing magnetic resonance imaging comprising a step of exciting nuclear spins in a body to be imaged, characterized in that said step is performed by carrying out a method. A magnetic resonance imaging scanner for carrying out such a method.

17 Claims, 4 Drawing Sheets

(51) Int. Cl.
*G01R 33/48* (2006.01)
*G01R 33/24* (2006.01)
*G01N 24/08* (2006.01)
*G01R 33/34* (2006.01)
*G01R 33/44* (2006.01)
*G01R 33/565* (2006.01)
*G01R 33/58* (2006.01)

(52) U.S. Cl.
CPC ............ *G01R33/4833* (2013.01); *G01N 24/08* (2013.01); *G01R 33/34046* (2013.01); *G01R 33/44* (2013.01); *G01R 33/4822* (2013.01); *G01R 33/5659* (2013.01); *G01R 33/586* (2013.01)

(56) References Cited

OTHER PUBLICATIONS

Cloos, M.A., et al.; "$K_t$ points: Fast Three-Dimensional Tailored RF Pulses for flip-angle homogenization over an extended volume"; [online]; [Retrieved on Jun. 30, 2011]; Retrieved from the Internet <URL: http://eta2.bio.cmu.edu/ISMRM/ISMRM%202010%20Stockholm/files/102_1458.pdf; 1 page.

Jankiewicz, M., et al.; "Practical considerations for the design of sparse-spokes pulses"; Journal of Magnetic Resonance; vol. 203; Issue 2; 2010; Publisher: Elsevier, Inc.; pp. 294-304.

Zelinski, A.C., et al.; "Sparsity-Enforced Slice-Selective MRI RF Excitation Pulse Design"; IEEE Transactions on Medical Imaging; vol. 27; Issue 9; Sep. 2008; pp. 1213-1229.

\* cited by examiner

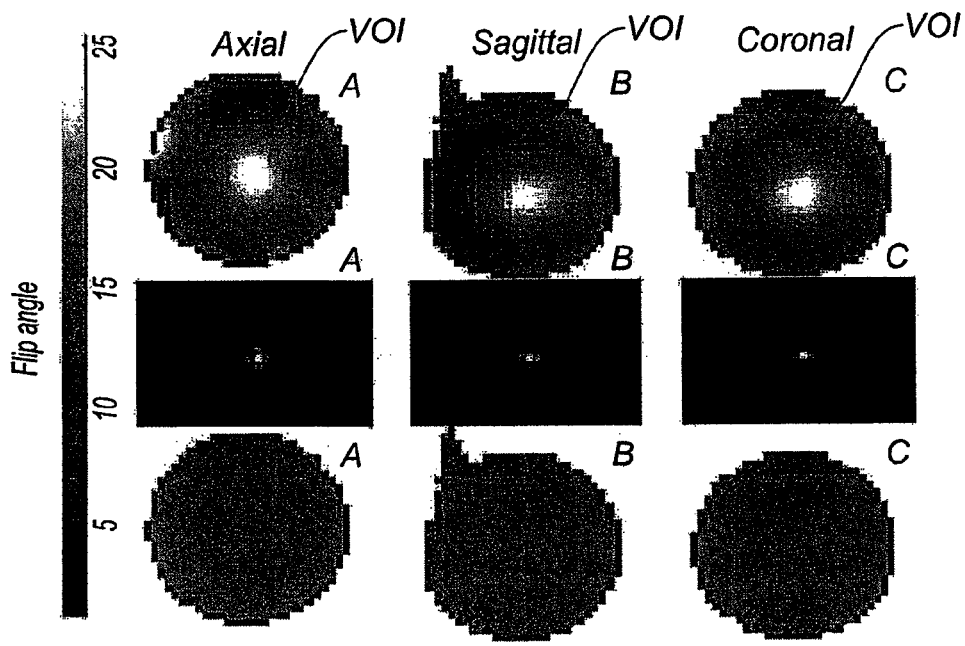
Fig. 3
Fig. 4
Fig. 5
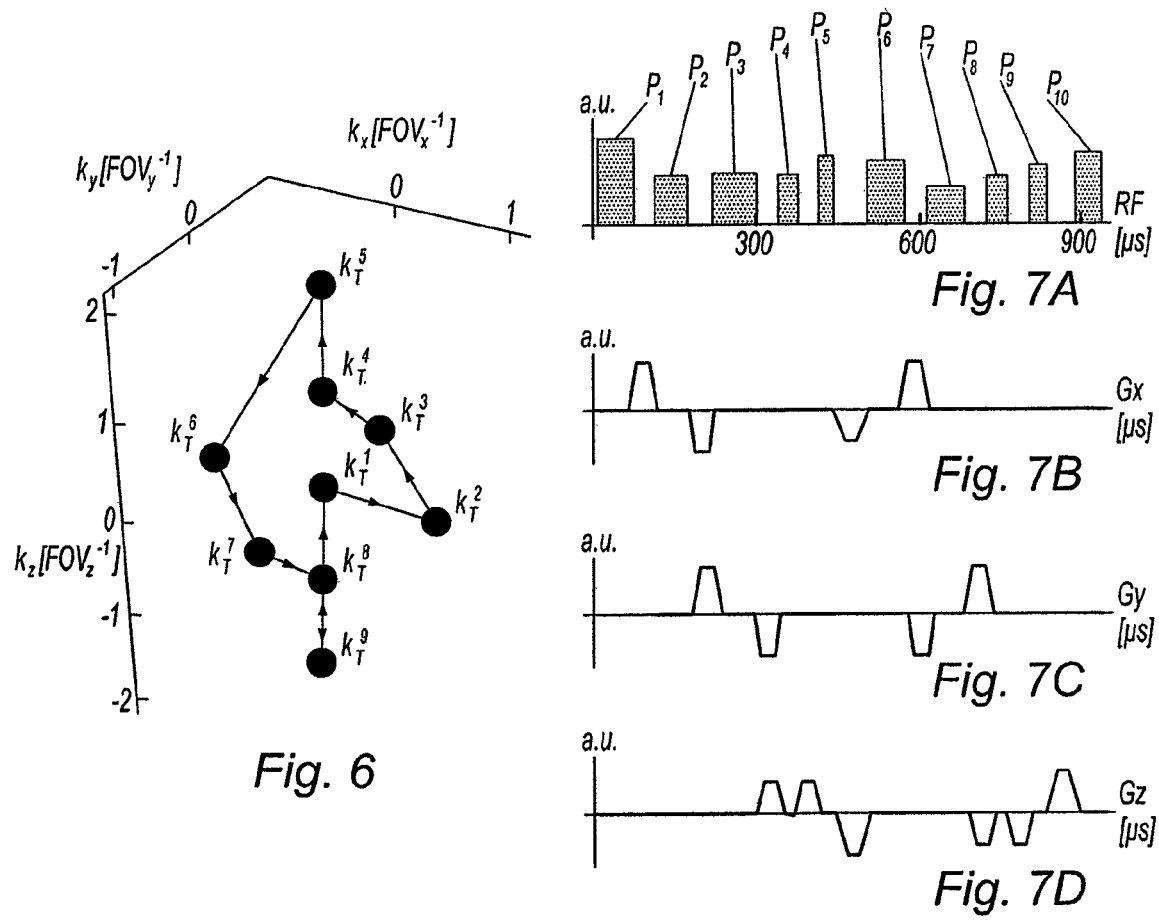
Fig. 6
Fig. 7A
Fig. 7B
Fig. 7C
Fig. 7D

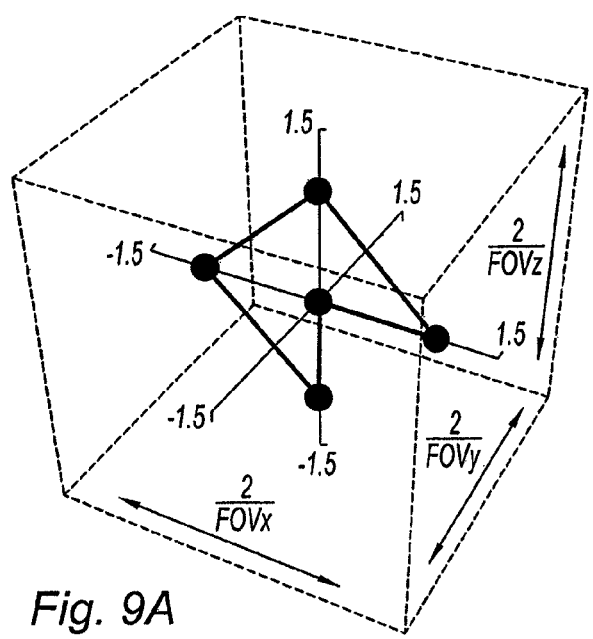
Fig. 9A
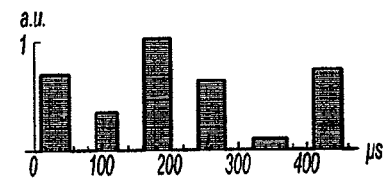
Fig. 9B
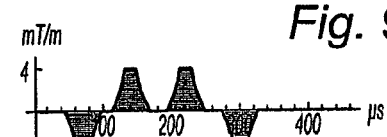
Fig. 9C
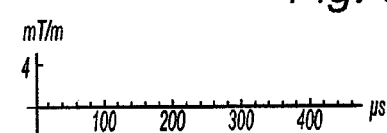
Fig. 9D
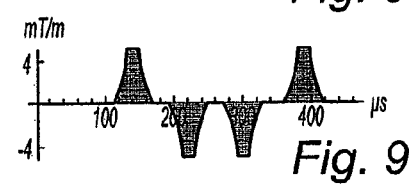
Fig. 9E
Fig. 10A 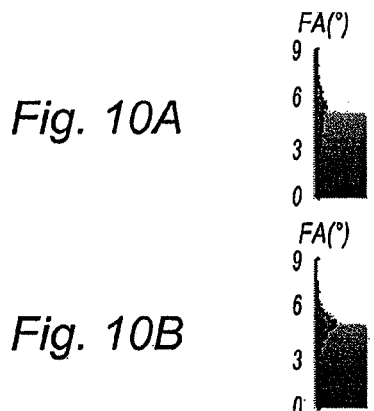 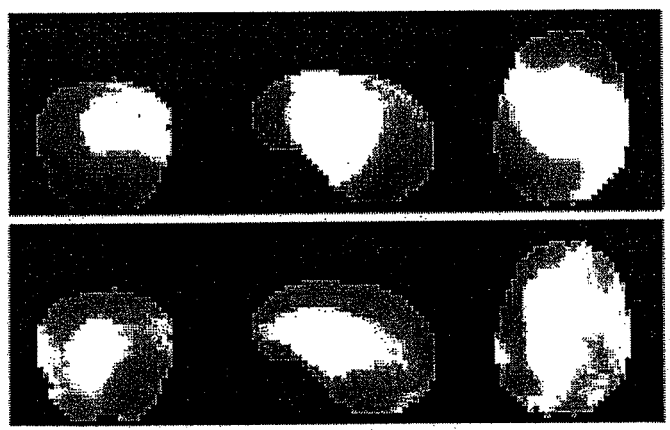
Fig. 10B 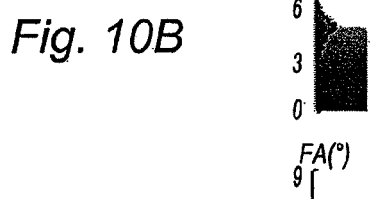 
Fig. 10C 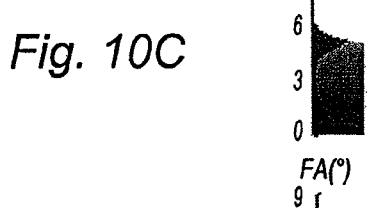 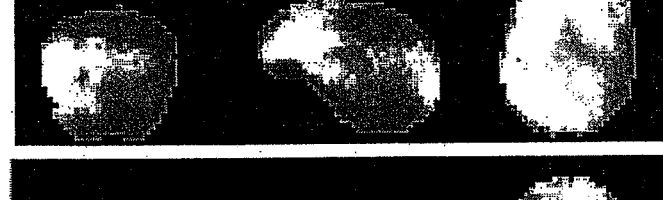
Fig. 10D  

METHOD AND APPARATUS FOR COMPENSATING FOR $B_1$ INHOMOGENEITY IN MAGNETIC RESONANCE IMAGING BY NONSELECTIVE TAILORED RF PULSES

FIELD OF THE INVENTION

The invention relates to a method for correcting the radio-frequency pulsed field (or "$B_1$") inhomogeneity in nuclear magnetic resonance (NMR), and more particularly in nuclear magnetic resonance imaging (MRI). The invention also relates to an apparatus, or "scanner", adapted for carrying out such a method.

BACKGROUND

Magnetic resonance imaging (MRI) is a very powerful tool in research and diagnostics. It comprises immerging a body in a static magnetic field $B_0$ for aligning nuclear spins thereof; exposing it to a transverse, circularly-polarized radio-frequency (RF) pulse $B_1$ at a resonance frequency known as the "Larmor frequency" for flipping said nuclear spins by a predetermined angle; and detecting a signal emitted by flipped nuclear spins, from which an image of the body can be reconstructed. Here, "transverse" means that the polarization plane of the RF pulse is perpendicular to the static magnetic field $B_0$, which is conventionally assumed to be aligned along a "z" axis.

There is a trend to move towards higher and higher static magnetic fields in order to improve the spatial resolution of MRI. For example, magnetic fields of 1.5 T (Tesla) are currently used in clinical practice, 3 T is the highest field used in commercial apparatuses, and research systems can operate at more than 7 T. However, as the strength of the static magnetic field increases, the wavelength of the radio-frequency pulse decreases and its amplitude distribution within the body to be imaged becomes less homogeneous.

Radio-frequency pulsed field inhomogeneities already introduce significant artifacts at 3 T. At 7 T, the Larmor frequency of protons is about 298 MHz, which corresponds to a wavelength around 14 cm in the human brain, i.e. a size comparable to that of a human head. In these conditions, the radio-frequency field spatial distribution is so inhomogeneous that images e.g. of a human brain obtained with standard techniques can become very difficult to interpret.

The $B_1$ inhomogeneity problem is so important that it could hinder further developments of high-resolution MRI.

A great number of techniques have been developed in order to compensate for $B_1$ inhomogeneity or, more generally, in order to excite nuclear spins according to a uniform excitation pattern.

Parallel transmission consists in using a plurality of antennas to generate the radio-frequency pulsed field $B_1$. In "static" parallel transmission ("RF shimming") the amplitude and initial phase on each antenna are adjusted in order to homogenize the RF field by interference. Instead "dynamic" parallel transmission, e.g. in the so-called "Transmit SENSE" technique [1], does not aim at homogenizing the instantaneous radio-frequency field, but only the resulting spin flip angle. In other words, the field may stay inhomogeneous at some given instant, but the temporal variation of the radio-frequency field finally yields the desired excitation pattern. With respect to static "RF shimming", dynamic parallel transmission allows homogenizing the flip angle over a much larger volume and reducing the electric energy left in the body as heat. However, all parallel transmission techniques have the drawback of adding hardware complexity. If parallel transmission is used as the sole strategy for counteracting $B_1$ inhomogeneity, either very complex excitation coils are required or a significant residual inhomogeneity has to be tolerated.

The "three-dimensional tailored pulses" approach [2, 3] uses time-varying magnetic gradients to navigate in the spatial-frequency domain ("k-space") along a predetermined trajectory whilst transmitting RF pulses.

In particular, document [2] relates to a method using a k-space trajectory in the form of a stack of spirals for achieving uniform excitation (i.e. flipping) of the spins within a region of interest of a body immerged in a uniform $B_0$ field. This method is penalized by lengthy RF pulse durations, making it impractical for clinical applications and bringing $B_0$-inhomogeneity and relaxation issues up front.

Document [3] describes a method using "spokes" trajectories with a static magnetic field gradient in a given direction to perform slice selection. This method only addresses flip-angle homogenization in the slice plane, and assumes $B_1$-inhomogeneities to be insignificant through the selected slice.

SUMMARY OF THE INVENTION

The invention aims at providing a method of exciting nuclear spins uniformly over an extended volume such as a human brain, overcoming at least part of the limitations of the prior art. The method of the invention is based on a strategy to find short non-selective tailored radio-frequency pulses; it does not require parallel transmission but can benefit from it, if available.

An object of the invention is then a method of exciting nuclear spins in a body comprising the steps of:

(a) immerging said body in a static magnetic field $B_0$ for aligning nuclear spins along a magnetization axis, said static magnetic field being substantially uniform over at least a volume of interest of said body;

(b) exposing said body, or at least said volume of interest, to a time-varying magnetic field gradient having components directed along at least three non-coplanar directions and to a transverse radio-frequency field ($B_1$), whereby said time-varying magnetic field gradient defines a three-dimensional trajectory in k-space constituted by segments linking discrete points, and said transverse radio-frequency field deposits radio-frequency energy along at least part of said trajectory for flipping said nuclear spins by a same predetermined flip angle, independently from their position within said volume of interest.

Magnetization field $B_0$ is "substantially uniform" in the sense that it is as uniform as it is reasonably possible, with no intentionally-introduced gradients. In practice, some spatial variation $\Delta B_0$ of this field is always present due to the magnetic susceptibility inhomogeneity of the body to be imaged. As it will be described below, this spatial variation can be accounted for in pulse design.

In particular, said time-varying magnetic field gradient can consist of a sequence of magnetic field gradient pulses. Even more particularly, said transverse radio-frequency field can comprise transverse radio-frequency subpulses interleaved with said magnetic field gradient pulses, whereby said radio-frequency subpulses deposit radio-frequency energy in said discrete points of k-space. Even more particularly, it is possible to only deposit radio-frequency energy in said discrete points of k-space, by avoiding applying a radio frequency field simultaneously to said magnetic field gradient pulses.

While the method of document [2] tries to perform a rather extensive sampling of k-space, resulting in very long pulses, the method of the invention is based on the excitation of a small number of carefully selected spatial frequency components. The method of document [3] also realizes a sparse sampling of the two-dimensional $k_x$-$k_y$ plane, but at the same time it performs a fast scan of segments along the $k_z$ axis due to the static slice-encoding gradient; moreover, as discussed above, this method is intrinsically slice-selective and does not allow flip-angle homogenization over an extended volume.

A unique feature of a method according to an embodiment of the invention is the fact that radio-frequency energy is deposited—exclusively or not—in discrete locations, or "$k_T$ points", of said k-space, corresponding to "stationary" points of the transmission k-space trajectory. In other words, in the method, according to said embodiment of the invention, a finite amount of energy is deposited at selected points of k-space where the k-space trajectory makes a short stop. Instead, in the methods of documents [2] and [3], radio-frequency energy is only deposited while moving along a line in k-space (a spiral in the $k_x$-$k_y$ plane for [2], a "spoke" along the $k_z$ axis for [3].

In particular, the deposit of radio-frequency energy can be purely discrete. In this case, no radio-frequency subpulse is applied simultaneously to the magnetic field gradient pulses. Alternatively a "hybrid" approach can be followed, wherein some radio-frequency energy is also deposited while moving between $k_T$ points. In limiting cases, it is possible to avoid stopping in $k_T$ points by continuously playing the gradients while going through them, and/or by continuously playing the radio-frequency field as the k-space trajectory is unwound. In any case, the important idea is, given a flip-angle inhomogeneity target residual spread, to keep the number of visited $k_T$ points as small as possible and to select the shortest possible trajectory across them. Advantageously, the k-space trajectory can be constituted by (approximately) straight segments linking the carefully-chosen $k_T$ points, corresponding to sharp "knees" or bends of the trajectory.

Another distinguishing feature of the inventive method is the fact that all the spatial directions (x, y and z), and therefore all the spatial frequency directions ($k_x$, $k_y$ and $k_z$) are treated essentially in a same way. Instead in the methods of documents [2] and [3], the k-space is sampled differently along the $k_z$ axis and in the $k_x$-$k_y$ plane.

Another object of the invention is a method of exciting nuclear spins in a human head, the method comprising the steps of:

(a) immerging said human head, or a portion thereof, in a static magnetic field for aligning nuclear spins along a magnetization axis substantially parallel to a cranio-caudal direction of said human head, said static magnetic field being substantially uniform over at least a volume of interest (VOI) of said human head;

(b) exposing at least said volume of interest, to a time-varying magnetic field gradient defining a bi-dimensional trajectory in k-space constituted by straight segments linking discrete points, and said radio-frequency non-selective pulse having a transverse polarization deposits radio-frequency energy along at least part of said trajectory; the positions of said discrete points in k-space being determined, and the radio-frequency non-selective pulse having a transverse polarization being designed, for flipping said nuclear spins by a same predetermined flip angle, independently from their position within said volume of interest.

More particularly, said time-varying magnetic field gradient can have a first component directed along said cranio-caudal direction and a second component directed along a left-right direction of said human head but no component directed along a ventro-dorsal direction of said human head.

Advantageously, said radio-frequency non-selective pulse having a transverse polarization can be radiated by a plurality of antennas arranged around said cranio-caudal direction.

Another object of the invention is a method of performing magnetic resonance imaging comprising a step of exciting nuclear spins in a body to be imaged, characterized in that said step is performed by carrying out a method as described above.

Still another object of the invention is a magnetic resonance imaging scanner comprising:

a magnet for generating a static magnetic field for aligning nuclear spins along a magnetization axis, said static magnetic field being uniform over at least a volume of interest of said body;

means for generating a transverse radio-frequency field and magnetic field gradient pulses, and for directing said subpulses toward said body; and means for detecting a signal emitted by flipped nuclear spins within said body or at least said volume of interest;

characterized in that said means for generating a transverse radio-frequency field and magnetic field gradient pulses comprise computing means for carrying out a method as described above.

BRIEF DESCRIPTION OF THE DRAWINGS

Additional features and advantages of the present invention will become apparent from the subsequent description, taken in conjunction with the accompanying drawings, which show:

FIGS. 3A-3C, three maps of the flip angle distribution along an axial, sagittal and coronal plane of a gel phantom immerged in a uniform magnetization field and exposed to a single non-selective (square) radio-frequency pulse;

FIGS. 4A-4C, three maps of the absolute differences between the Fourier transforms of the flip angle distributions of FIGS. 3A-3C and the Fourier transforms of ideally uniform excitations;

FIGS. 5A-5C, three maps of the flip angle distribution along said axial, sagittal and coronal planes of said gel phantom, obtained by applying the method of the invention;

FIG. 6, a k-space trajectory corresponding to a method according to an embodiment of the invention;

FIG. 7A, a plot of the power of the radio-frequency subpulses used in said embodiment of the invention;

FIGS. 7B, 7C and 7D, plots of the magnetic field gradients along three orthogonal axes (x, y and z, respectively) used in said embodiment of the invention to define the k-space trajectory of FIG. 6;

FIG. 9A, a k-space trajectory corresponding to a method according to another embodiment of the invention;

FIG. 9B, a plot of the power of the radio-frequency subpulses used in said embodiment of the invention;

FIGS. 9C, 9D and 9E, plots of the magnetic field gradients along three orthogonal axes (x, y and z, respectively) used in said embodiment of the invention to define the k-space trajectory of FIG. 9A; and FIGS. 10A-10D the results of a comparative test for evaluating the performances of said embodiment of the invention.

DETAILED DESCRIPTION

Figure 1:
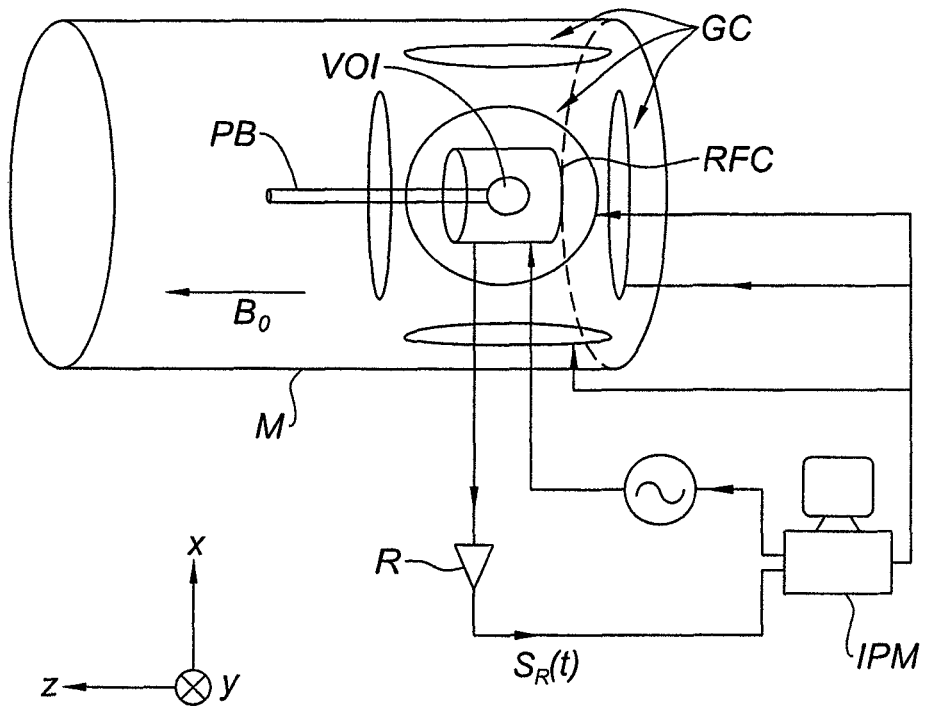
FIG. 1, a functional diagram of a magnetic resonance imaging scanner for carrying out a method according to the invention.

FIG. 1 represents—very schematically—a magnetic resonance imaging (MRI) scanner comprising:
- a magnet M for generating a static and substantially uniform magnetic field $B_0$, oriented along direction z, in which is immersed a patient body (or a part of it) PB to be imaged;
- a radio-frequency coil RFC for exposing said body to transverse radio-frequency pulses ("transverse" here means having a polarization which is perpendicular to $B_0$, and therefore lying in a x-y plane) and for detecting signal emitted by flipped nuclear spins within said body;
- three sets of gradient coils GC for generating gradient fields, i.e. magnetic fields directed along the z direction which vary linearly along a respective spatial direction across the volume of interest (VOI);
- an oscillator OS, a modulator and an RF amplifier for generating radio-frequency pulses which feed the radio-frequency coil. In parallel transmission, the radio-frequency modulator and amplifier are duplicated as many times as there are transmit channels;
- a receiver R for amplifying said spin resonance signal before demodulating and digitizing it. In parallel imaging, the preamplifiers and receivers are duplicated as many times as there are receive channels ; and
- information processing means IPM driving the oscillator OS, the radio-frequency coils RFC and the gradient coils; and for receiving and processing the resonance signal $S_R(t)$ amplified by the receiver R. The information processing means IPM can be a computer —or a set of electronic programmable computers—comprising at least a memory for storing a computer program (i.e. a piece of executable code) and a least one processor for executing said program. The hardware part of the scanner can be conventional, while the software is adapted for carrying out the method of the invention. Therefore software means—e.g. code stored on a computer-readable storage medium such as a CD-ROM—can turn a standard scanner into a device according to the invention, without any need for hardware modifications.

Figure 2:
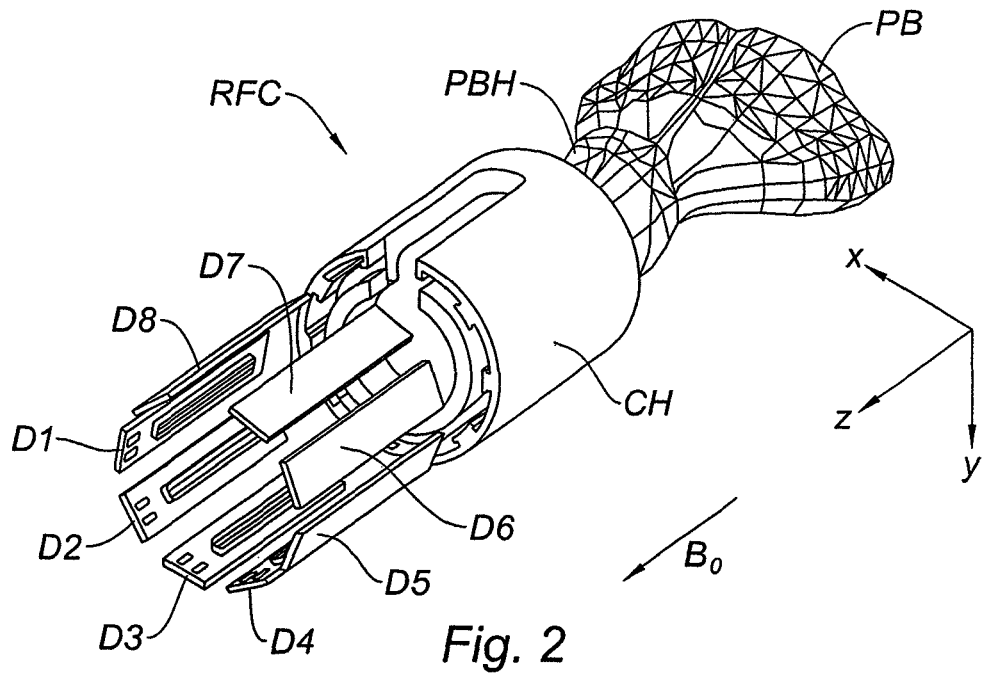
FIG. 2, a multi-dipole head coil suitable for parallel transmission and used to implement an embodiment of the invention.

FIG. 2 illustrates a radio-frequency coil adapted for carrying out a method according to an embodiment of the invention. This coil is particularly suited for imaging a human head. It behaves as an 8-channel transceiver and comprises a cylindrical insulating housing CH (internal diameter of 27.6 cm), which can contain a head part PBH of a patient body PB, with a slot intended to be positioned in front of the eyes of the patient (this is not essential). Eight strip-line dipoles D1-D8 are distributed every 40° inside this housing. The dipoles are identical to each other and have independent driving circuits (not represented) so that they can radiate linearly polarized electromagnetic fields having independently defined amplitudes and phases. It should be understood that any other MRI coil can be used for carrying out the invention. The same coil can be used for transmitting and receiving RF signals, as in the embodiment described here, or separate transmit and receive coils can be used.

The method of the invention is based on a new and highly-efficient strategy for single-shot k-space 3D-coverage in transmission, which limits the RF pulse duration while keeping amplitude levels compatible with human safety and SAR (Specific Absorption Rate) regulations. The method produces non selective RF pulses which homogenize the nuclear spin flip angle (FA) over substantial volumes. It is inspired by existing methods using "three-dimensional tailored pulses", such as those described in references [2] and [3]. Its novelty lies, in particular, in the use of pulses ("blips") of magnetic field gradients along three orthogonal—or, more generally: non coplanar—directions to navigate in the 3D k-space, and in the transmission of RF in stationary k-space locations, called "$k_T$-points", where energy is particularly needed to fight the RF inhomogeneities. Square subpulses played in $k_T$-points can have variable durations to allow for an ideal compromise between total pulse length and SAR minimizations.

FIGS. 3A-3C show grayscale maps of the flip angle distribution along an axial (1A), sagittal (1B) and coronal (1C) plane of a spherical gel phantom (diameter: 16 cm) immerged in a uniform 7 T magnetization field $B_0$ and exposed to a single non-selective (square) transverse, circularly polarized radio-frequency ($B_1$) pulse tuned at the Larmor frequency of the water proton (298 MHz at 7 T). The circularly polarized (CP) pulse is obtained by driving the eight dipoles D1-D8 with identical amplitudes and with initial phases equal to their respective azimuth angle. The gel phantom has the same dielectric permittivity and electrical conductivity as an average human head.

The amplitude and duration of the radio-frequency subpulses are chosen in such a way that, if the $B_1$ distribution within the phantom were uniform, the nuclear spins of the protons would be flipped by 15°; otherwise stated, the target flip angle ($FA_{Target}$) is 15°. The figures show that the actual flip angle (FA) distribution is significantly inhomogeneous, with a NRMSE (normalized root mean square error) of 23% and flip angle values varying from 4.9° to 23.3°.

The FA maps of FIGS. 3A-3C were obtained by using the Actual Flip Angle acquisition sequence (AFI) [4] driven with square pulses. In addition to these maps, additional echoes were acquired within the same sequence to measure the spatial variation of the main magnetic field ($\Delta B_0$) from the phase evolution between echoes [5]. This $\Delta B_0$ inhomogeneity map can subsequently be used to refine the tailored pulse design, but is not the subject of the invention.

FIGS. 4A-4C show grayscale maps of the absolute differences between the Fourier transform of the flip angle distributions of FIGS. 3A-3C and the Fourier transform of an ideally uniform excitation ($FA(x,y,z)=FA_{Target}$) over a 132-mm slab chosen along the z-axis for FA homogenization, this VOI dimension corresponding roughly to the axial height of an adult brain.

These figures show that the difference of the Fourier transform of the homogeneous target distribution of the FA and its distribution obtained with a standard circularly polarized (CP) mode yields dominant frequency components clustered around the center of k-space. These spatial frequencies are specifically the ones to be addressed in order to compensate for $B_1$-inhomogeneities.

According to the method of the invention, FA homogenization can be obtained within the VOI by driving the RF-coil and the gradient coils with a sequence of subpulses describing an excitation k-space trajectory which specifically compensates for the $B_1$-inhomogeneity. For this reason it will be called hereafter "compensation trajectory". In the meantime, the difference between the CP-mode image and the uniform target excitation will be called "compensation pattern".

One idea at the basis of the invention is that an approximately uniform FA distribution can be obtained by using a simple transmission k-space trajectory only comprising a small number N of discrete spatial frequency components, typically less than 10, around the center of k-space, instead of performing an extended sampling of k-space as taught by document [2]. This allows a significant reduction of the pulse duration. As it will be discussed below, use of parallel transmission allows a further reduction of the pulse duration, down to less than a millisecond in the context of the presented setup.

As discussed above, in an alternative embodiment of the invention, radio-frequency power can also be deposited whilst moving in-between $k_T$-points. It is even possible to not stop at the selected $k_T$-points and continuously play the gradients while going across the $k_T$-sites. The induced additional reduction in pulse duration depends on what amount of energy needs to be deposited at the various sites. Typically, these reductions in pulse duration come at the price of an increase in SAR, which can limit the applicability for fast sequences. In the end, the overall k-space trajectory may be a hybrid concatenation of stationary $k_T$-points interlaced with rapid crossings to provide an optimal balance between SAR minimization and pulse duration.

The $k_T$ points—or at least some of them—are advantageously chosen as corresponding to the N most energetic components of the three-dimensional Fourier transform of said compensation pattern, sampled over a discrete grid.

FIG. 6 shows a k-space trajectory comprising nine $k_T$ points $k_T^1$-$k_T^9$ (black spheres). Seven of these points ($k_T^1$-$k_T^5$, $k_T^7$, $k_T^8$) correspond to the seven most energetic Fourier components of the difference (FIGS. 4A-4C) between the three-dimensional Fourier transform of the flip angle distribution induced by a simple CP mode (FIGS. 3A-3C) and the three-dimensional Fourier transform of a uniform distribution over the VOI. Apart from the central position in k-space, these $k_T$-points typically correspond to the face centers of a parallelepiped centered in k-space, whose side size is roughly $(2/\lambda_{obj})$, where $\lambda_{obj}$ is the RF wavelength in the object to be imaged, in each of the three spatial directions. In the present case, since the object to be imaged (a human brain) has a size of the same order of magnitude than the RF wavelength, $\lambda_{obj}$ is taken to be equal to a field of view FOV which exceeds only slightly the dimensions of said object, which in turn coincides with the VOI. In this case, the parallelepiped has size 2/FOV.

In some cases less than six $k_T$-points can be used, e.g. three central points of nonparallel faces of said parallelepiped centered in k-space. The parallelepiped can also be slightly shifted with respect to the center of the k-space; but it should contain said center, i.e. the point $k_x=k_y=k_z=0$.

Two additional $k_T$ points ($k_T^6$, $k_T^9$) have been selected along $k_z$ at distances 2/FOV from the center of k-space. These additional $k_T$-points were found to enhance the performance. While the Fourier transform method indicated relatively large contributions at these additional points, they were not the points with the next highest amplitude. An explication of the improved performance with these additional points will be discussed later.

In the example of FIG. 6, the k-space trajectory begins and ends in $k_T^1$ whose coordinates are: $k_x=k_y=k_z=0$.

FIGS. 7B, 7C and 7D show temporal plots of the magnetic field gradient pulses (or "blips") $G_x$, $G_y$ and $G_z$, aligned along axes x, y and z respectively, which were used to define the k-space trajectory of FIG. 6. In order to be able to span the k-space, gradient pulses have to be applied along three non-coplanar, and preferably mutually perpendicular, directions. It is not essential that one of these directions coincide with the magnetization axis (z). Segments connecting adjacent $k_T$-points are not necessarily oriented along the x, y or z axis; for moving in k-space along an oblique segment, two ($G_x$, $G_y$; $G_x$, $G_z$; $G_y$, $G_z$) or even three ($G_x$, $G_y$, $G_z$) gradient pulses have to be applied simultaneously.

The gradient pulses were generated by a Siemens AC84 gradient head coil, allowing gradient amplitudes up to 50 mT/m and a slew rate of 333 T/m/s; the rising and falling fronts of the pulses are clearly visible on the figures. If the gradients are played continuously while transmitting RF power, i.e. if the k-space trajectory does not comprise "stops" in the $k_T$-points, the gradient pulses are not as well-separated as on FIG. 2; in a limiting case, they lose their identity and merge in a more or less continuous, time-varying magnetic field gradient.

The Fourier method is particularly advantageous, but it is not the only available method for finding a compensation pattern and placing the $k_T$ points. Other methods, which have been developed for the two-dimensional problem of spoke placement in slice-selective methods, may also be applied to $k_T$-points placement. See e.g. the so-called "sparsity-enforced" method disclosed by [6].

Having placed the $k_T$-points, the next step is to connect them by segments so as to cover all points with minimum travel. Then comes the design of the RF transverse field to be applied to the body between the gradient blips and/or simultaneously with them. Here we consider the case where RF energy is only deposited at the $k_T$ point: therefore, RF energy is only provided in the form of RF subpulses interleaved with (and not overlapped to) the gradient pulses.

Square RF subpulses $P_1$-$P_{10}$ have been used. Although this is not an essential feature of the invention, this choice is considered optimal because of their broadband characteristics and because such subpulses have the best shape to reach a given integral (i.e. flip angle) while minimizing SAR (which varies as the time integral of the squared amplitude of the subpulse).

The head coil RFC comprises several (eight) independent coil elements (dipoles), thus allowing the use of parallel transmission in order to assist homogenization of the FA distribution. Each dipole emits, between two consecutive gradient blips, a square RF subpulse having amplitude and phase which can be different from that of the subpulses emitted by the other dipoles. However, these subpulses are emitted simultaneously and have the same duration. This is not essential, but strongly recommended. As it can be easily understood, if one dipole emitted a shorter subpulse than the other dipoles, this would increase SAR without shortening the overall duration of the excitation sequence; therefore it would be advantageous to lengthen this subpulse while reducing its amplitude to keep its integral constant. If one dipole emitted a subpulse longer than the others, this would increase the overall duration of the sequence with minimal benefit in terms of SAR: therefore it would be advantageous to either shorten this subpulse—to reduce duration—or to lengthen the other subpulses—to reduce SAR. In any case, the optimal solution consists in transmitting pulses with a same duration.

While pulses transmitted by different coil elements at a given time have the same duration, pulses transmitted at different times (i.e. depositing energy at different $k_T$-points) can have different durations.

Design of the RF excitation subpulses for the eight channels of the head coil can be performed by using the Small Tip Approximation in the spatial domain [7], which considers channel-dependant transmit $B_1$ profiles as well as $B_0$ spatial variations within the VOI. Moreover the local variable exchange method [8] can advantageously be applied to solve the Magnitude Least Squares problem, which alleviates the unnecessary phase homogenization constraint. The application of these techniques for designing RF pulses using parallel transmission is rather well-known; they work for any arbitrary, predefined k-space trajectory compatible with the gradient hardware; and $k_T$-points placement and linkage do provide such a k-space trajectory.

The excitation pulses thus obtained contain sub-optimal $k_T$-point subpulse durations. Indeed, for all MRI applications, there is a tradeoff between SAR and the overall pulse duration. Longer pulses can have negative effects on image quality. On the other hand, reducing the length requires higher peak amplitude to obtain the same flip-angle. While this can be beneficial for some applications, it also increases the SAR proportionally to the square of the RF wave amplitude. With the spatial domain method [7], the $\Delta B_0$-related phase evolution can be taken into account during pulse design. For this purpose, the duration $\delta t_j$ of each of the j individual subpulses of the excitation sequence must be specified beforehand. In order to minimize the duration of these subpulses while keeping relatively low power requirements, a simple iterative optimization procedure can be implemented. First, a relatively arbitrary duration is set for all subpulses. By applying the spatial domain method, a set of amplitudes is found for each of the excitation pulses. Given a maximum allowed peak amplitude ($P_{Lim}$), the pulse durations can be rescaled by using the following equation:

$$\delta t_j^{New} = \frac{\text{Max}\{P_i\}_j}{P_{Lim}} \delta t_j^{Old} + \Delta$$

where $P_i$ indicates the amplitude found on the ith channel. In the specific example considered here, $P_{Lim}$ was the maximum voltage available on the transmit channels (170 V). But it could be rescaled down to a maximum value corresponding to local and global SAR constraints. The constant $\Delta$ ideally should be 0. In practice however, it is often helpful to relax this constraint in the optimization procedure by including a small $\Delta$. Directly applying the optimized $\delta t_j^{New}$ to the previously found excitation pulses results in incorrect $\Delta B_0$-induced-phase compensation. Simply redesigning the excitation pulse with the newly found subpulse duration allows a new excitation pulse to be found including the appropriate corrections. The new pulse can have a slightly different power distribution over time. Therefore, it might be necessary to repeat this procedure several iterations until the optimization criteria have been met.

FIG. 7A shows a temporal plot of the total RF power summed over all 8 transmit channels. It can be seen that in this particular case, no RF pulsing occurs while the magnetic field gradients are on.

The use of parallel transmission and the particular structure of the RF coil can explain why it has been advantageous to introduce, in the k-space trajectory, two additional $k_T$ points along the $k_z$ direction even if they did not correspond to the $8^{th}$ and $9^{th}$ highest-energy spatial frequency components of the compensation pattern. The locations of the eight transmit strip lines of the coil only differ by their azimuth. This means that parallel transmission introduces additional degrees of freedom to fight RF inhomogeneity only in the transverse plane, and not in the axial (z) direction; but this is ignored by the Fourier method for $k_T$ point placement, where only a CP mode is considered. To compensate for this misbalance, it is advantageous to introduce extra $k_T$-points along $k_z$. A further segmentation of the coil along z with independent $z_+$ and $z_-$ strip line elements could potentially avoid requiring these extra $k_T$-points. Another possible cause for this requirement is the influence of the $\Delta B_0$ distribution, not taken into account during Fourier-based $k_T$-point identification.

RF-pulse design has been described in the framework of the small-tip approximation, which allows linearization of the Bloch equation. However, several known techniques allow overcoming this limitation; see e.g. [9-12]. These techniques may be applied to the method of the invention.

Figure 8:
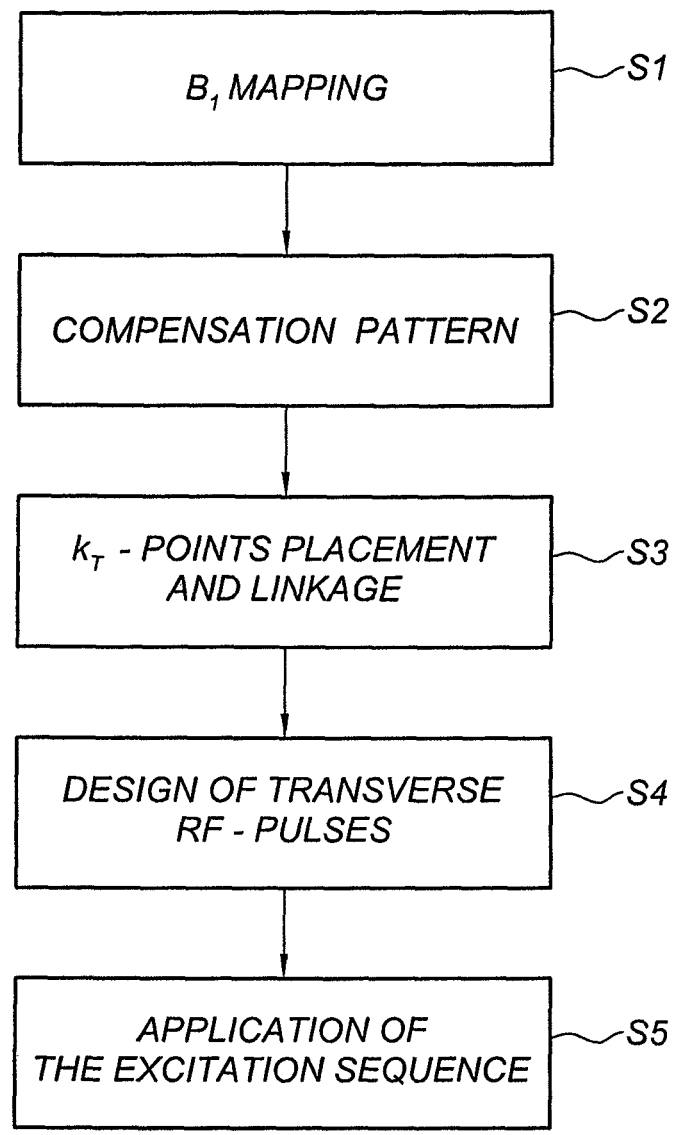
FIG. 8, a flow-chart of a method according to an embodiment of the invention.

FIG. 8 shows a simplified flow-chart of a method according to the invention.

A first step S1 consists in mapping FA inhomogeneity or, equivalently, $B_1$ inhomogeneity. A $B_0$ map can also be acquired for later better pulse design.

A second step S2 consists in determining a compensation pattern, to achieve a target uniform excitation pattern despite inhomogeneity.

A third step S3 consists in placing $k_T$-points in k-space according to said compensation pattern, and in linking these points to yield a short excitation k-space trajectory. Use of parallel transmission allows a reduction of the number of $k_T$-points necessary to achieve a satisfactory homogenization of the excitation pattern, at least along some directions depending on the layout of the transmitting coil elements.

A fourth step S4 consists in determining the RF subpulses to deposit energy along the k-space trajectory determined by the $k_T$-points. This step can comprise an iterative optimization of the subpulse durations. Again, it may use parallel transmission, or not.

A fifth step S5 consists in applying the excitation sequence to the body to be imaged.

FIGS. 5A-5C illustrate the result achieved by the method of the invention. They are FA maps obtained with the AFI sequence by replacing standard square pulses by the subpulse sequence designed by the method described above.

Targeting a 15° FA resulted in a 950-µs excitation pulse, which produced a 7.3% NRMSE (normalized root mean square error over the volume of interest), i.e. 15±1.1°. Compared to the CP mode (23% NRMSE), the Max/Min FA was reduced from 23.3/4.9° to 18.0/11.4°. Comparing experimental results with full Bloch simulations returned a correlation factor of 99.7%, indicating excellent agreement between theory and experiment. Optimization of the pulse durations converged to a minimum after 3 iterations. Based on the performance of an Intel core 2 duo 2.4-Ghz with 4-GB RAM, the pulse design could be performed in roughly 5 minutes.

The pulses generated according to this embodiment of the invention could advantageously be used as small excitations in short-TR 3D sequences such as FLASH or MP-RAGE.

The method of the invention has been developed for medical applications, and in particular for high-magnetic field (>3 T) MRI of the human brain. However, the method can also be applied to other medical and nonmedical MRI techniques (e.g. oil prospection), to nuclear magnetic resonance (NMR) spectroscopy and more generally to all techniques which require a uniform spatial distribution of the nuclear spin excitation within the volume of a sample.

To show the validity of the method, it was applied to homogenize the FA over the entire brain of three volunteers, at 7 T, by implementation on a transmit-array system with 8 independently-driven channels.

Experimental validation was performed on a Siemens 7 T Magnetom scanner (Erlangen, Germany), equipped with an 8-channel transmit array (1 kW peak power per channel). The head gradient set allowed amplitudes up to of 50 mT/m and a slew rate of 333 mT/m/ms. The target flip-angle was 5°. For both RF transmission and reception, a transceiver-array head coil having a structure similar to that illustrated on FIG. 2 was used, consisting of 8 stripline dipoles distributed every 42.5-degrees on a cylindrical surface of 27.6-cm diameter, leaving a small open space in front of the subject's eyes. All dipoles were tuned ideally to the proton Larmor frequency at 7 T and matched identically to a 50Ω line impedance.

The brain volume was first extracted from initial images acquired with a fast sequence. Subsequent to the Fourier transform of the 3D brain mask, the $k_T$-point locations were determined by the position of the N largest magnitude components in k-space. As anticipated from the earlier phantom studies discussed above, it was found the low spatial components dominate k-space. Bloch simulations indicated that 5 $k_T$-points were sufficient to achieve spatial excitation uniformity better than 10% in the human brain. Surprisingly, it was found that the 5 $k_T$-point lies in the $k_x$-$k_z$ plane, where z is the cranio-caudal direction (coinciding with the orientation of the static magnetic field $B_0$) and x the left-right direction. Otherwise stated, a satisfactory homogenization of spin flip angles could be achieved within a human brain by using a bi-dimensional trajectory in k-space, represented on FIG. 9A; FIGS. 9C, 9D and 9E represent the corresponding $G_x$, $G_y$ and $G_z$ gradient pulses or "blips", respectively; the "blips" have a duration of 40 μs each; it can be seen that $G_y$=0. The choice of only 5 $k_T$-points was advantageous as it allowed reducing the pulse duration, and therefore the SAR, with respect to the case of the phantom, where a three-dimensional trajectory in k-space was found to be necessary to reach comparable homogeneity performance.

Then, pulse design was performed using the small tip approximation in the spatial domain, and the local variable exchange method to solve the magnitude least squares (MLS) problem. The six optimized square RF-pulses are represented on FIG. 9B.

These solutions were typically found in 3 to 4 iterations of the pulse duration optimization procedure. Based on the performance of an Intel core 2 duo 2.4-Ghz with 4-GB RAM, the complete pulse design procedure could be performed in roughly 30 s.

The flip angle distribution measured in subject n° 1 is illustrated on FIG. 10C (central coronal, sagittal and axial brain cross sections; a flip-angle (FA) histogram is superposed on the gray scale). FIG. 10D shows the corresponding distribution obtained by numerical simulations; it can be seen that the agreement between theory (10D) and experiment (10C) is quite good, even if the experimental flip-angle distribution is slightly broader than the theoretical one. FIG. 10B shows the experimental results obtained using a static shim sequence, corresponding to a single $k_T$-point optimized at the center of the k-space. It can easily be seen that the FA distribution is significantly larger than in the case of FIG. 10C; yet, the total RF energy required was roughly the same (within 10%) in both cases; the total energy in the static shim case could have been further reduced, but it would have remained of the same order of magnitude. FIG. 10A corresponds to the use of a standard CP (circularly polarized) pulse, leading to a broad distribution of flip angles between 2° and 8°.

References

[1] "Transmit SENSE", U. Katscher, P. Bornert, C. Leussler, J S van den Brink, Magnetic Resonance in Medicine, vol. 49, pp 144-150 (2003).

[2] "Small Tip Angle Three-Dimensional Tailored Radiofrequency Slab-Select Pulse for Reduced $B_1$ Inhomogeneity at 3 T", S. Saekho et al., Magnetic Resonance in Medicine 53:479-484 (2005).

[3] "Fast-$k_z$ Three-Dimensional Tailored Radiofrequency Pulse for Reduced $B_1$ Inhomogeneity", S. Saekho et al., Magnetic Resonance in Medicine 55:719-724 (2006).

[4] "Actual Flip-Angle Imaging in the Pulsed Steady State: A Method for Rapid Three dimensional Mapping of the Transmitted Radiofrequency field", V. L. Yarnykh, Magnetic Resonance in Medicine, vol. 57:192-200 (2007).

[5] "MAFI Sequence: simultaneous cartography of $B_0$ and $B_1$," Amadon A. et al., ISMRM 16:1248 (2008).

[6] "Sparsity-enforced slice-selective MRI RF excitation pulse design", A. C. Zelinski et al., IEEE Transitions in Medical Imaging 27: 1213-1228 (2008).

[7] "Spatial domain method for the design of RF pulses in multicoil parallel excitation", W. Grissom, C-Y Yip, Z. Zhang, A. Stenger, J. A. Fessler, D. C. Noll, Magnetic Resonance in Medicine, vol. 56, pp 620-629 (2006).

[8] "Magnitude Least Squares Optimization for Parallel Radio Frequency Excitation Design Demonstrated at 7 Tesla With Eight Channels", K. Setsompop, L. L. Wald, V. Alagappan, B. A. Gagoski, E. Adalsteinsson, Magn. Reson. Med. 59: 908-915 (2008).

[9] "High-flip-angle slice-selective parallel RF transmission with 8 channels at 7 T", K. Setsompop et al., Journal of Magnetic Resonance 195:76-84 (2008).

[10] "Additive Angle Method for Fast Large-Tip-Angle RF Pulse Design in Parallel Excitation", W. A. Grissom et al., Magnetic Resonance in Medicine 59:779-787 (2008).

[11] "Designing Mutichannel, Multidimensional, Arbitrary Flip Angle RF Pulses Using an Optimal Control Approach", D. Xu et al., Magnetic Resonance in Medicine 59:547-560 (2008).

[12] "Fast Large-Flip-Angle Multidimensional and Parallel RF Pulse Design in MRI", W. A. Grissom et al., IEEE Transactions on Medical Imaging, 28,10:1548-1559 (2009).

The invention claimed is:

1. A method of exciting nuclear spins in a body, the method comprising the steps of:
   (a) immerging said body (PB) in a static magnetic field ($B_0$) for aligning nuclear spins along a magnetization axis (z), said static magnetic field being substantially uniform over at least a volume of interest (VOI) of said body;
   (b) exposing said body, or at least said volume of interest, to a time-varying magnetic field gradient having components ($G_x$, $G_y$, $G_z$) directed along at least three non-coplanar directions (x, y, z) and to a radio-frequency spatially non-selective pulse having a transverse polarization ($B_1$), whereby said time-varying magnetic field gradient defines a three-dimensional trajectory in k-space constituted by straight segments linking discrete points ($k_T^1$-$k_T^9$), and said radio-frequency spatially non-selective pulse having a transverse polarization deposits radio-frequency energy along at least part of said trajectory; the positions of said discrete points in k-space being determined, and the radio-frequency spatially non-selective pulse having a transverse polarization being designed, for flipping said nuclear spins by a same predetermined flip angle, independently from their position within said volume of interest.

2. A method according to claim 1 wherein said time-varying magnetic field gradient consists of a sequence of magnetic field gradient pulses.

3. A method according to claim 2 wherein said radio-frequency spatially non-selective pulse having a transverse polarization comprises transverse radio-frequency subpulses ($P_1$-$P_{10}$) interleaved with said magnetic field gradient pulses, whereby said radio-frequency subpulses deposit radio-frequency energy in said discrete points of k-space.

4. A method according to claim 3 wherein no radio frequency pulse is applied simultaneously to said magnetic field gradient pulses, whereby radio-frequency energy is only deposited in said discrete points of k-space.

5. A method according to claim 1, comprising using a plurality of independently driven antenna elements ($D_1$-$D_8$) for generating and applying said radio-frequency spatially non-selective pulse having a transverse polarization.

6. A method according to claim 1, further comprising a preliminary step of determining said discrete points of k-space and the corresponding amount of radio-frequency energy by computing a three-dimensional Fourier transform of a predetermined excitation pattern, called a compensation pattern.

7. A method according to claim 6 wherein said preliminary step comprises the substeps of:
  i. defining said volume of interest where a uniform target distribution of the nuclear spins' flip angle is wanted;
  ii. determining the distribution of the nuclear spins' flip angle induced by a standard circularly polarized radio-frequency mode in said volume of interest; and
  iii. taking, as said compensation pattern, the difference between said uniform target distribution of the nuclear spins flip angle and the distribution of the nuclear spins flip angle induced by said standard circularly polarized radio-frequency mode.

8. A method according to claim 7 wherein said substep ii. is performed by measurement.

9. A method according to claim 6 wherein said preliminary step further comprises determining at least some of said discrete points of excitation k-space as corresponding to a number of the most energetic components of the three-dimensional discrete Fourier transform of said compensation pattern.

10. A method according to claim 7 wherein said preliminary step further comprises a step of iteratively computing the phase and amplitude of said transverse radio-frequency subpulses, or of the contribution to said transverse radio-frequency subpulses generated by each of said independently driven antenna elements, in order to minimize the overall duration of application of said radio-frequency field under SAR constraints.

11. A method according to claim 1 wherein at least some of said discrete points of k-space belong to face centers of a parallelepiped containing the center of k-space and whose side size is approximately $(2/\lambda_{obj})$, where $\lambda_{obj}$ is the RF wavelength in the body to be imaged.

12. A method according to claim 1 wherein said time-varying magnetic field gradient consists of a sequence of magnetic field gradient pulses directed along three perpendicular directions, one of which is parallel to said magnetization axis.

13. A method according to claim 1 wherein said radio-frequency spatially non-selective pulse having a transverse polarization is constituted by a sequence of square subpulses each corresponding to one of said discrete points of excitation k-space, or to a segment linking two of said points.

14. A method of exciting nuclear spins in a human head, the method comprising the steps of:
  (a) immerging said human head, or a portion thereof, in a static magnetic field for aligning nuclear spins along a magnetization axis substantially parallel to a cranio-caudal direction of said human head, said static magnetic field being substantially uniform over at least a volume of interest (VOI) of said human head;
  (b) exposing at least said volume of interest, to a time-varying magnetic field gradient defining a bi-dimensional trajectory in k-space constituted by straight segments linking discrete points, and said radio-frequency spatially non-selective pulse having a transverse polarization deposits radio-frequency energy along at least part of said trajectory; the positions of said discrete points in k-space being determined, and the radio-frequency spatially non-selective pulse having a transverse polarization being designed, for flipping said nuclear spins by a same predetermined flip angle, independently from their position within said volume of interest.

15. A method according to claim 14 wherein said time-varying magnetic field gradient has a first component directed along said cranio-caudal direction and a second component directed along a left-right direction of said human head but no component directed along a ventro-dorsal direction of said human head.

16. A method according to claim 14, wherein said radio-frequency spatially non-selective pulse having a transverse polarization is radiated by a plurality of antennas arranged around said cranio-caudal direction.

17. A method of performing magnetic resonance imaging comprising a step of exciting nuclear spins in a body to be imaged, characterized in that said step is performed by carrying out a method according to claim 1.

* * * * *